United States Patent
DeLa Torre Bueno

(10) Patent No.: US 7,678,581 B2
(45) Date of Patent: *Mar. 16, 2010

(54) CORRELATING CHEMICAL AND SPATIAL DATA WITHIN PATHOLOGY SAMPLES

(75) Inventor: Jose DeLa Torre Bueno, Vista, CA (US)

(73) Assignee: Clarient, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/021,267

(22) Filed: Jan. 28, 2008

(65) Prior Publication Data

US 2009/0191544 A1 Jul. 30, 2009

(51) Int. Cl.
    *G01N 33/566* (2006.01)
(52) U.S. Cl. ...................................... 436/501; 436/503
(58) Field of Classification Search .................. 436/501
    See application file for complete search history.

(56) References Cited

U.S. PATENT DOCUMENTS

| 6,150,508 | A | * | 11/2000 | Murphy et al. | ............ 530/387.1 |
| 6,986,748 | B2 | * | 1/2006 | McAlister et al. | ............ 600/564 |
| 2002/0132246 | A1 | * | 9/2002 | Kallioniemi et al. | ............ 435/6 |
| 2004/0085443 | A1 | * | 5/2004 | Kallioniemi et al. | ........ 348/135 |

* cited by examiner

*Primary Examiner*—Ann Y Lam
(74) *Attorney, Agent, or Firm*—Fish & Associates, PC

(57) ABSTRACT

A tissue sample to be analyzed is tested. Multiple different samples of multiple areas of said tissue sample, each of said multiple areas is a smaller area than an entire tissue sample to be analyzed. After analysis, the tissue sample is processed in a way that facilitates viewing tumor information on the sample, for example, by fixing or staining. An area is identified on the stained sample, and at least one of the samples that corresponds to an identified area is tested. This small area is tested using a technique that homogenizes the sample before testing.

8 Claims, 3 Drawing Sheets

CORRELATING CHEMICAL AND SPATIAL DATA WITHIN PATHOLOGY SAMPLES

BACKGROUND

Different techniques can be used to characterize pathology samples such as tumors. One of such techniques investigates homogenized samples and determines information from the homogenized sample, e.g., within a test tube, and the other collects spatially orientated information.

Homogenized tissue sample tests can test for different characteristics—however, the whole contents of the test tube is averaged for the test. Tests of these types include polymerase chain reaction or PCR, Western blotting that can be used to quantify concentrations of types of proteins in a sample, DNA arrays, that can be used to quantify the amount of DNA in specified sequences, RNA arrays that can be used to quantify specific sequences of messenger RNA and thus determine the expression level of many different genes, and others. These kinds of tests can be very specific—for example, quantitative PCR can be used to determine the relative level of sequences that differ by only a single mutation. However, the specificity is reduced since the test is measuring over the entire sample.

Staining techniques can also be used. In slide based tests the sample is sectioned into thin sections (typically 5 microns) and placed on a microscope slide for observation with a microscope, photo microscopy or image analysis. Stains are used on the tissue to make certain features visible. One stain is the classic H&E stain. This stain allows pathologists to view the overall morphology of a tissue and identify areas of tumor based on morphological features that show up under the stain. Other stain techniques produce other results. For example, an IHC (Immunohistochemistry) reagent is a custom antibody to a given target which can be a protein or other chemical linked (either before or after it attaches to its target) to a stain that will be visible in the microscope. This marker might be an enzyme which will catalyze a color generating reaction. IHC can be used to visualize contents of a slide to determine that a target molecule is present. IHC can also be used to specify the specific cells or even sub cellular structures in which the target molecule is present. By using several distinguishable stains linked to different antibodies, it is possible to characterize the extent of co-localization of several targets or determine that they are found in different cells or organelles.

FISH (Fluorescent in-situ hybridization) can locate the position on a chromosome of a given genetic sequence by using several probes linked to different colored dyes. Fish makes it possible to see the spatial relationship of different loci. For instance FISH can be used to detect chromosome translocation that cause leukemia by marking two loci known to be brought together by a translocation that causes leukemia with red and green fluorochromes. If the translocation has occurred, these 2 probes will be brought next to each other and will appear to be a single yellow dot. Thus FISH can produce detailed spatial data on the location of gene sequences.

In general, the operation on homogenized tissue make many measurements of different targets but are in effect averaging over the entire block that was homogenized. This has limited their utility in practical diagnosis because the tissue sample delivered to a pathologist is rarely entirely cancer. In cancer surgery, the goal is to remove tissue until the margins are clear (that is free of cancer). In biopsy samples, there is often no way to assure that only tumor is sampled. Further, it is known that many cancers are themselves genetically and metabolically heterogeneous. This means that the numbers produced by all of the homogenization methods may be averages of tumor and non tumor tissue or different regions of the tumor.

Slide based methods overcome the localization limitations but suffer from restrictions on the number of chemical species that can be detected at once. While DNA arrays can test for thousands of sequences at once, FISH is restricted to 4 or 5 probes at a time. Similarly IHC is limited by the number of stains that can be attached and visualized, e.g., 3 or 4.

These limitations mean that in practice it is possible to know the amount of various types of DNA, RNA and protein in a tissue in detail but not the precise location of those species or it is possible to know the location of a few species with high spatial accuracy.

Other techniques collect spatially oriented information from slides. Laser capture microdissection, for example, uses a laser to release a chosen section of the tissue, e.g. while observing the tissue on a slide under a microscope (with no cover slip). The released sample is captured in a vial, and the localized sample is tested using one of the homogenization methods mentioned above. This allows obtaining test information for a known location. While this is difficult at the sub cellular level, it is possible to select one or a few cells that are known to be part of a tumor.

Laser capture microdissection has not been widely used because of its disadvantages. One is the cost and complexity of the equipment involved. Also, since the sample is collected after it has been fixed and possibly stained these processes may disrupt the target molecules and prevent some chemical methods from operating correctly. Also, since the size of the area sampled is inherently limited by the collection technique, it may be too small relative to the tumor that is to be characterized.

SUMMARY

The present inventors recognize that the averaging over multiple areas may provide disadvantages and may not accurately represent the specific way that a tumor grows and is reviewed. For example, tumors often grow with finger-like projections through the tissue. It may be desirable to obtain localized portions of tissue sample, and test those localized portions using one of the homogenizing techniques disclosed above.

DETAILED DESCRIPTION

Figure 1:
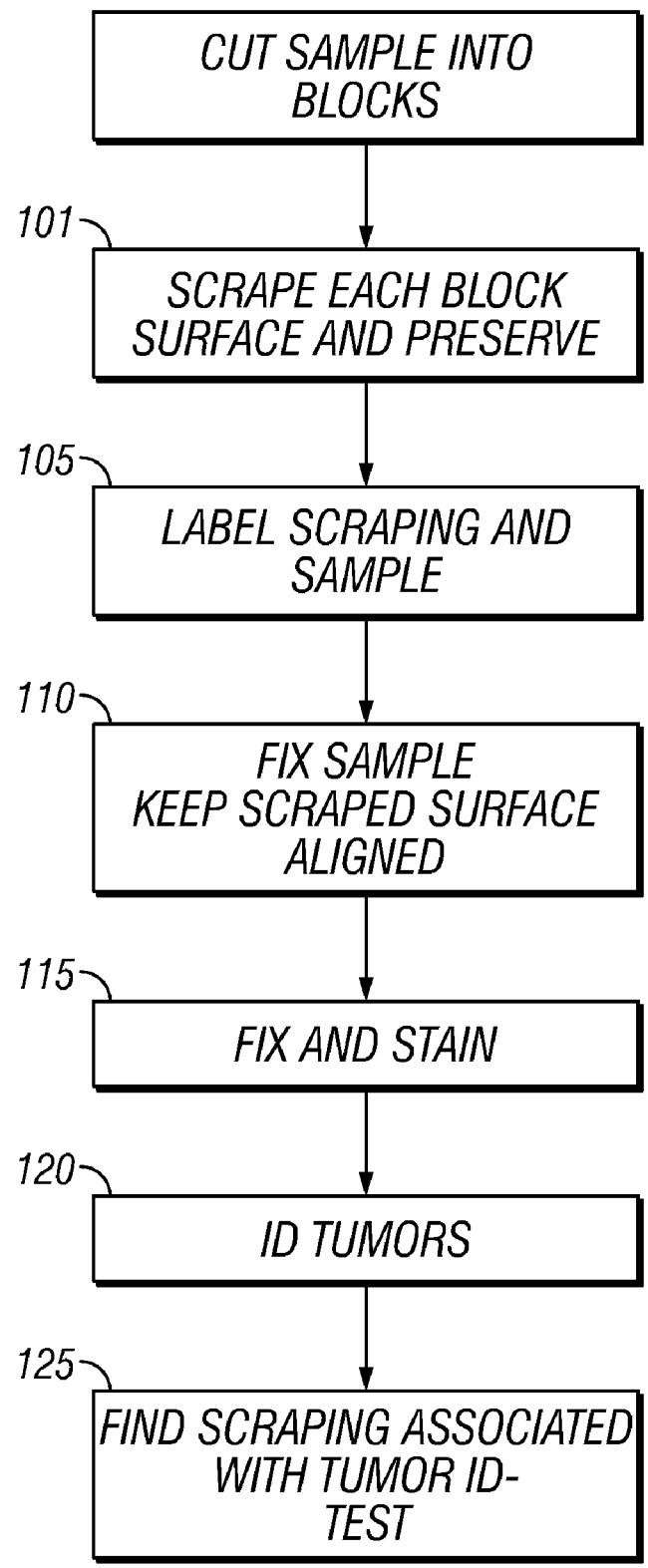
FIG. 1 shows a flowchart of operation.

The present application recognizes that the goal of cancer surgery is often to remove tissues until the margins of the removal are entirely clear and free of cancer. However, homogenized samples cannot assure that only tumor is being sampled. This becomes more difficult when one considers that the cancers are themselves genetically and metabolically heterogeneous. This means that the values produced by tests which are homogenizing tests, may be averages between tumorous and non-tumorous tissues, or may be averages between different areas of the tumors.

The technique disclosed herein collects a number of different samples or cells at a number of different areas. The collected samples/cells are analyzed using a homogenization method. Any of the different homogenization methods discussed above may be used for this purpose. However, since the sample is sampled in different divided locations, localized sample areas can be used in these different divided locations.

The system operates as follows, and according to the flowchart of FIG. 1. At 100, the sample is first delivered to the so-called grossing station and cut into blocks. This is the station where the sample is prepared for further analysis. The cutting can be carried out using naked eye or under a scope.

At 101, a scraping from the surface of each block is taken and preserved. However, in the embodiment, the area is sampled using a special sampling technique described herein. Each of the samples is placed in a vial of preservative suitable for homogenization. For example, the samples may be fixed in paraffin, or the like.

At 105, both the preserved sample and the scraping are labeled with a label allowing the parts to be identified with one another.

At 110, the labeled sample is placed in a fixation cassette, taking special care to maintain the scraped surface as being the outer surface in the microtome.

115 carries out fixing, embedding, mounting, staining and section of the blocks in the usual way. Any staining appropriate for the specific detection method that is selected can be used in this way.

At 120, each of the slides is examined under a microscope to identify tumor areas or other analysis. The slides can be automatically examined, e.g., with an image analyzer, if appropriate. Based on the analysis at 120, areas found to have a tumor can be identified. That identification is then used to find the scraping of that sample as carried out at 101, and analyze that scraping using a selected homogenization technique.

An advantage of this technique is that the homogenization method can be carried out only on a specific area which has been found to have the tumor, and that area identified in advance. Since the homogenization analysis can be expensive, this technique may minimize the cost by only testing samples that are pre-detected to have likely tumors. Moreover, artifacts and difficulties introduced by fixation and staining may be reduced since the scraping samples are collected before that fixation and staining.

A second embodiment uses a special tool described with reference to FIGS. 2A and 2B. A sampling tool 200 shown in FIG. 2A collects an array of samples from a surface of the tissue block to be examined. The sampling tool 200 includes a number of sampling ends 201 which can be scrapers, brushes or hypodermic needles, for example. Any of these collection devices collects a small number of cells from the location that they touch. In essence, the sampling tool 100 samples the entire area described by the perimeter of the tool, but each of the individual sampling elements 101 obtains only a very small location within that outer perimeter. The tool may be of a similar size to a usual sample slide, e.g., a 4 mm square. This may vary, and other sizes can also be used.

Figure 2A:
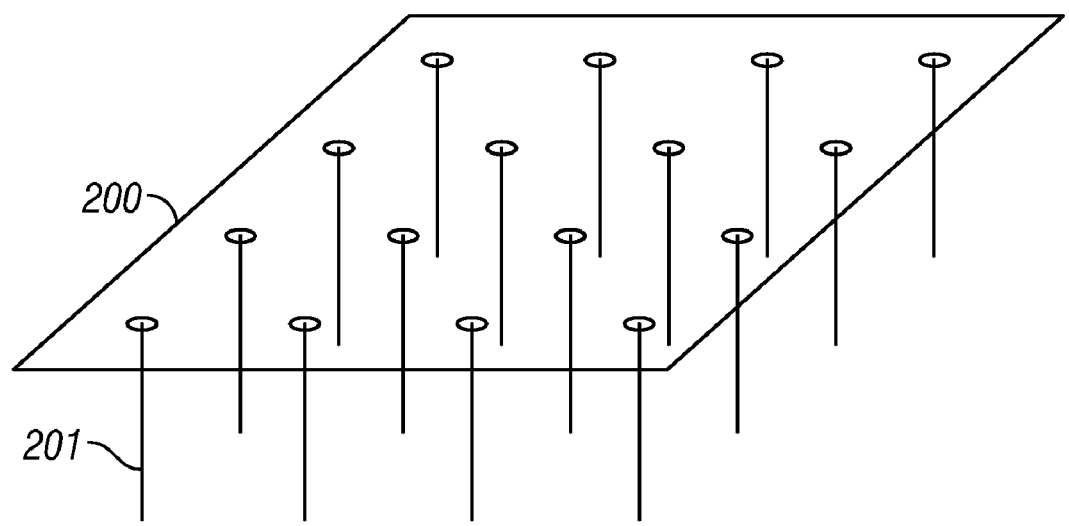
FIGS. 2A and 2B illustrate a sampling tool.
Figure 2B:
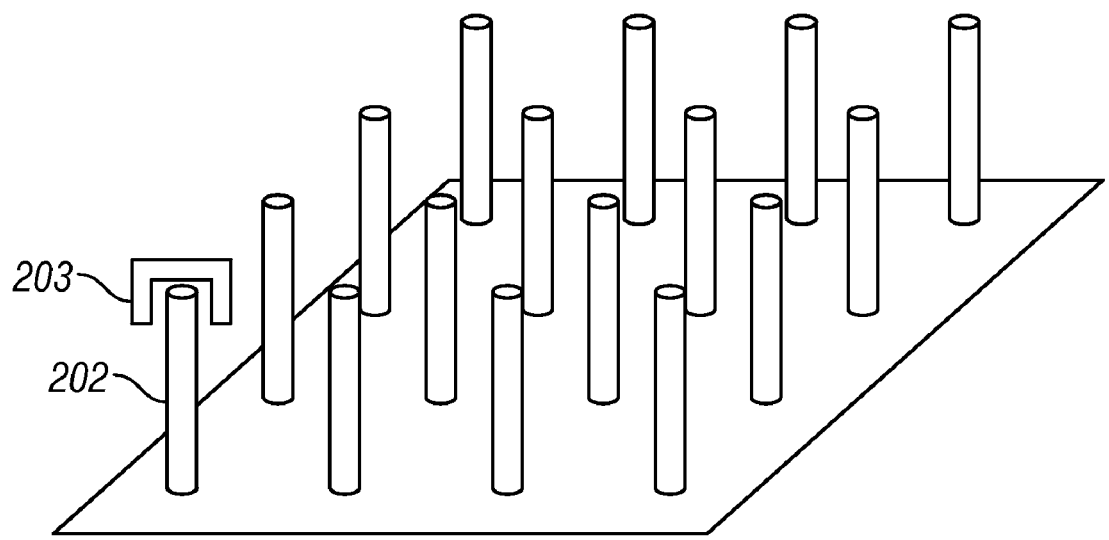

FIG. 2B shows the sampling vials 202 in an arrangement which matches with the sampling tool 200. The sample vials 202 are fastened together in an array that matches with the array, having the same spacing and geometric arrangement as the sampling members 201.

Once sampled, the sampling ends 201 can be slid into the vials 202. Another array of caps 203 may also be provided to cover the individual vials 202. Each vial stores a sample that is geometrically coordinated with an area on the overall sample.

FIGS. 2A and 2B show 4×4 samplings to sample 16 points on the surface of the tissue block. However, other spacings can similarly be used.

This embodiment uses a similar technique to that in FIG. 1. After sampling with the tool 200, the samples are stored. The block is then analyzed, via fixing and staining as usual. The pathologist identifies areas of interest within the block. Those areas of interest are coordinated to one or more specific samples taken by the sampling tool. The interesting region has a finer granularity, so in addition to identifying the block with the tumor to be sampled, the pathologist also identifies the region of the block and its corresponding sample point. The vial 202 corresponding to that block and point are then further analyzed using the homogenizing sample technique. However, since that vial is representative of a much smaller portion, the test is also much more specific.

In one embodiment, the tubes 201 may be formed with stops therein, to penetrate to a very shallow depth, for example 50μ. Other embodiments may further simplify the relationship between the sampled points and the selected interesting regions. For example, if the sampling method leaves holes in the block, such as would be done with an array of needles, then the first sections cut will have corresponding holes. These sections can be sectioned and stained using a generic stain such as H & E in the reference slide showing the locations of the samples. The locations of interest can be identified on the slide. Other techniques can also project locations of interest from another slide to the one slide.

Figure 3:
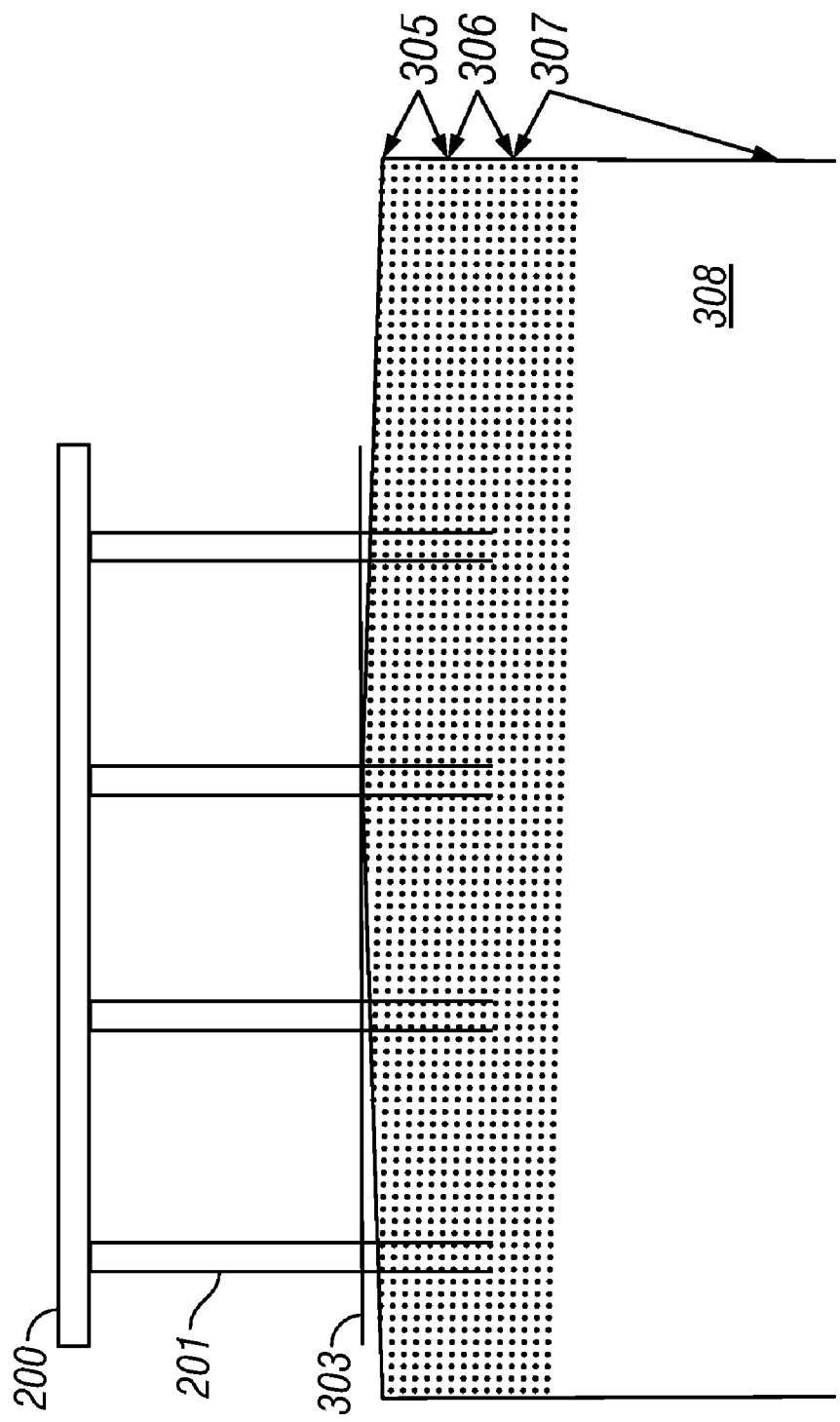
FIG. 3 shows a sampling operation.

FIG. 3 illustrates the sampling tubes embedded in a block, showing where the samples will be taken. This shows the tool 200, and the tubes 201, and shows how this is pushed into the sample block 308 up to the stop layer 303. This way, the sample tubes each collect a small sample of the block 308. The dotted lines in the FIG. 3 indicate where the sections will be cut when the block is mounted. The first section 305 is cut to face the block, e.g. from a face parallel to the travel of the tool. The next section 106 will have the impression of the sample array and can be used as a guide for the next set sampled locations. The next samples such as 107 can be continued however appropriate for tests being performed.

Alignment may be maintained by using a sample array that is non-symmetrical to prevent the sections from being flipped. For example one of the sampling devices can be left out, or a different size sampling device can be used on one side or an extra one used on one side relative to the other. In addition, the sampling device might have one or more sections that are non-symmetrical in their geometric arrangement.

The tubes 100 may use pressure in the hypodermic to collect and release the sample. If all these tubes are connected to a manifold, then mild suction can be used to make sure that each tube collects a sample; and pressure can be applied to release the samples into the collection vials.

In this way, a homogenization style analysis method can still be used. However, smaller areas are analyzed, to obtain spatial location and orientation information from the tests.

According to an embodiment, each of the sampling items is given a designation, such as A1, B2, and the like, in an attempt to maintain the proper positions of those devices.

The general structure and techniques, and more specific embodiments which can be used to effect different ways of carrying out the more general goals are described herein.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other data formats, other kinds of scales, etc, may be used.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be an Intel (e.g., Pentium or Core 2 duo) or AMD based computer, running Windows XP or Linux, or may be a Macintosh computer. The computer may also be a handheld computer, such as a PDA, cellphone, or laptop.

The programs may be written in C or Python, or Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attached Storage (NAS), or other removable medium or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

What is claimed is:

1. A method comprising:
    obtaining a previously excised tissue sample to be analyzed;
    first isolating multiple different portions from multiple different locations of said tissue sample, each of said multiple locations being smaller than the entire tissue sample to be analyzed;
    after said first isolating, processing said excised tissue sample in a way that facilitates visualizing tumor information on said sample;
    identifying an area of interest within said processed tissue sample using microscopic evaluation after said processing of said tissue sample; and
    selecting and testing at least one of said portions, wherein selecting is based on the tumor information in the area of interest.

2. A method as in claim 1, wherein said first isolating uses a tool that takes the multiple different portions spaced from one another.

3. A method as in claim 1, wherein said processing comprises staining the excised tissue sample.

4. A method as in claim 1, wherein said testing comprises using a test that homogenizes the at least one of said portions as part of the testing.

5. A method as in claim 4, wherein said testing uses PCR, Western blotting, a DNA array or an RNA array.

6. A method as in claim 2, wherein said multiple different portions have asymmetrical arrangement relative to each other.

7. A method as in claim 1, further comprising maintaining an orientation of said multiple different portions, with a specified surface of said multiple different locations all facing in a same direction.

8. A method as in claim 7, wherein said taking multiple samples comprises contacting a surface of the tissue sample, and wherein a contacted surface orientation is maintained in a specified way.

* * * * *